(12) United States Patent
Ogawa et al.

(10) Patent No.: US 8,681,095 B2
(45) Date of Patent: Mar. 25, 2014

(54) OPERATION INPUT UNIT AND MANIPULATOR SYSTEM

(75) Inventors: Ryohei Ogawa, Tokyo (JP); Kosuke Kishi, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/943,456

(22) Filed: Nov. 10, 2010

(65) Prior Publication Data

US 2011/0234484 A1 Sep. 29, 2011

(30) Foreign Application Priority Data

Mar. 29, 2010 (JP) .................................. 2010-75378

(51) Int. Cl.
*G09G 5/00* (2006.01)
*A61B 1/00* (2006.01)

(52) U.S. Cl.
USPC ............................... 345/156; 345/8; 600/103

(58) Field of Classification Search
USPC ................................................. 600/101–106
See application file for complete search history.

(56) References Cited

U.S. PATENT DOCUMENTS

| | | | | |
|---|---|---|---|---|
| 5,491,510 | A * | 2/1996 | Gove | 348/77 |
| 5,876,325 | A * | 3/1999 | Mizuno et al. | 600/102 |
| 5,911,036 | A * | 6/1999 | Wright et al. | 700/259 |
| 6,101,038 | A * | 8/2000 | Hebert et al. | 359/618 |
| 6,333,753 | B1 * | 12/2001 | Hinckley | 715/768 |
| 7,907,166 | B2 * | 3/2011 | Lamprecht et al. | 348/43 |
| 2006/0119539 | A1 * | 6/2006 | Kato et al. | 345/8 |
| 2006/0284792 | A1 * | 12/2006 | Foxlin | 345/8 |
| 2008/0234866 | A1 * | 9/2008 | Kishi et al. | 700/259 |
| 2010/0066821 | A1 * | 3/2010 | Rosener et al. | 348/77 |
| 2011/0238079 | A1 * | 9/2011 | Hannaford et al. | 606/130 |

FOREIGN PATENT DOCUMENTS

| | | |
|---|---|---|
| JP | 05-011713 | 1/1993 |
| JP | Hei 05-304646 | 11/1993 |
| JP | Hei 09-149339 | 6/1997 |
| JP | 2004-105539 A | 4/2004 |
| JP | 2007-029232 A | 2/2007 |
| JP | 2007-071782 | 3/2007 |
| JP | 2009-279193 A | 12/2009 |

\* cited by examiner

*Primary Examiner* — Alexander S Beck
*Assistant Examiner* — Ibrahim Khan
(74) *Attorney, Agent, or Firm* — Scully, Scott, Murphy & Presser, P.C.

(57) ABSTRACT

Unintended motion of a displayed object is prevented by rapidly detecting a state in which an operator becomes unable to operate an operating unit. Provided is an operation input unit including a display; a head-mounted unit; an operating unit to which an operating signal for a displayed object displayed on the display is input; a relative-position detecting section that detects the relative position between the head-mounted unit and the operating unit; and a control unit that controls the displayed object by switching between a first control mode in which the motion of the displayed object is controlled in accordance with an operating signal input to the operating unit and a second control mode in which the motion of the displayed object is controlled by limiting an operating signal input to the operating unit on the basis of the relative position detected by the relative-position detecting section.

20 Claims, 9 Drawing Sheets

OPERATION INPUT UNIT AND MANIPULATOR SYSTEM

BACKGROUND OF THE INVENTION

1. Field of the Invention

The present invention relates to an operation input unit and a manipulator system.

This application is based on Japanese Patent Application No. 2010-075378, the content of which is incorporated herein by reference.

2. Description of Related Art

Known head mounted displays (HMD) clear the field of view of wearers whose views are obstructed or notify the wearers of an abnormality when an outside abnormality is detected (for example, refer to Japanese Unexamined Patent Application, Publication No. Hei 5-304646 and Japanese Unexamined Patent Application, Publication No. Hei 9-149339).

When a wearer manipulates a displayed object, such as a device, displayed on the HMD with an operating unit in his or her hand, it sometimes becomes impossible for the wearer to operate the operating unit because the wearer suddenly changes his or her posture or releases the operating unit for some reason. Furthermore, when a wearer manipulates the operating unit in an orientation inclined toward the operating unit due to carelessness or the like, the vertical and lateral directions of the device or the like to be manipulated on the HMD and the manipulating direction of the operating unit sometimes become mismatched.

BRIEF SUMMARY OF THE INVENTION

It is an object of the present invention to provide an operation input unit and a manipulator system capable of rapidly detecting a state in which an operator becomes unable to normally operate the operating unit and capable of preventing unintended motion of a displayed object.

The present invention provides the following solutions to achieve the above object.

A first aspect of the present invention is an operation input unit including a display; a head-mounted unit mounted on the head of an operator; an operating unit to which an operating signal for a displayed object displayed on the display is input by the operation of the operator; a relative-position detecting section that detects the relative position between the head-mounted unit and the operating unit; and a control unit that controls the displayed object by switching between a first control mode in which the motion of the displayed object is controlled in accordance with an operating signal input to the operating unit and a second control mode in which the motion of the displayed object is controlled by limiting an operating signal input to the operating unit, on the basis of the relative position detected by the relative-position detecting section.

A second aspect of the present invention is a manipulator system including the operation input unit described above; a manipulator that is the displayed object; and an observation unit that acquires an image of the displayed object to be displayed on the display.

DETAILED DESCRIPTION OF THE INVENTION

An operation input unit 1 and a manipulator system 100 according to a first embodiment of the present invention will be described below with reference to FIGS. 1 to 8.

Figure 1:
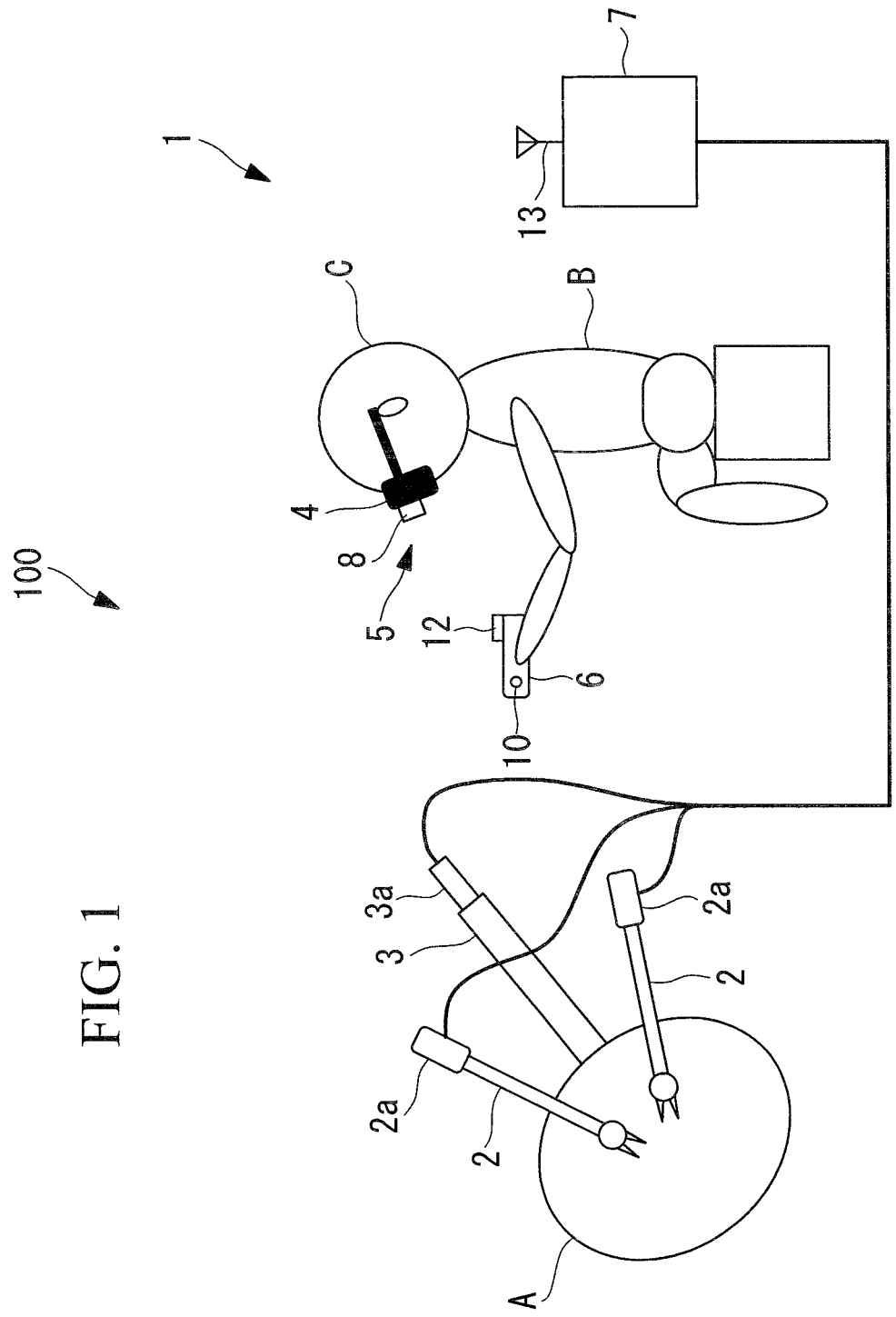
FIG. 1 is a diagram showing the overall configuration of an operation input unit and a manipulator system according to a first embodiment of the present invention.

The manipulator system 100 according to this embodiment is used for surgical procedures. As shown in FIG. 1, the manipulator system 100 includes a manipulator (displayed object) 2 to be inserted into the body of a patient A, an endoscope (observation unit) 3 that acquires an image of the manipulator 2, and the operation input unit 1 according to this embodiment.

The manipulator 2 can be changed in orientation, position, and operating state with a motor 2a. The endoscope 3 can be changed in orientation, position, and operating state with a motor 3a.

The operation input unit 1 is equipped with a HMD (head-mounted unit) 5 having a display section 4 (display) and mounted on the head C of an operator B, an operating unit 6 operated by the operator B, and a control unit 7 that moves the manipulator 2 based on the operation of the operating unit 6.

The display section 4 displays an image of the manipulator 2 in the body of the patient A, acquired by an endoscope 3.

Figure 2:
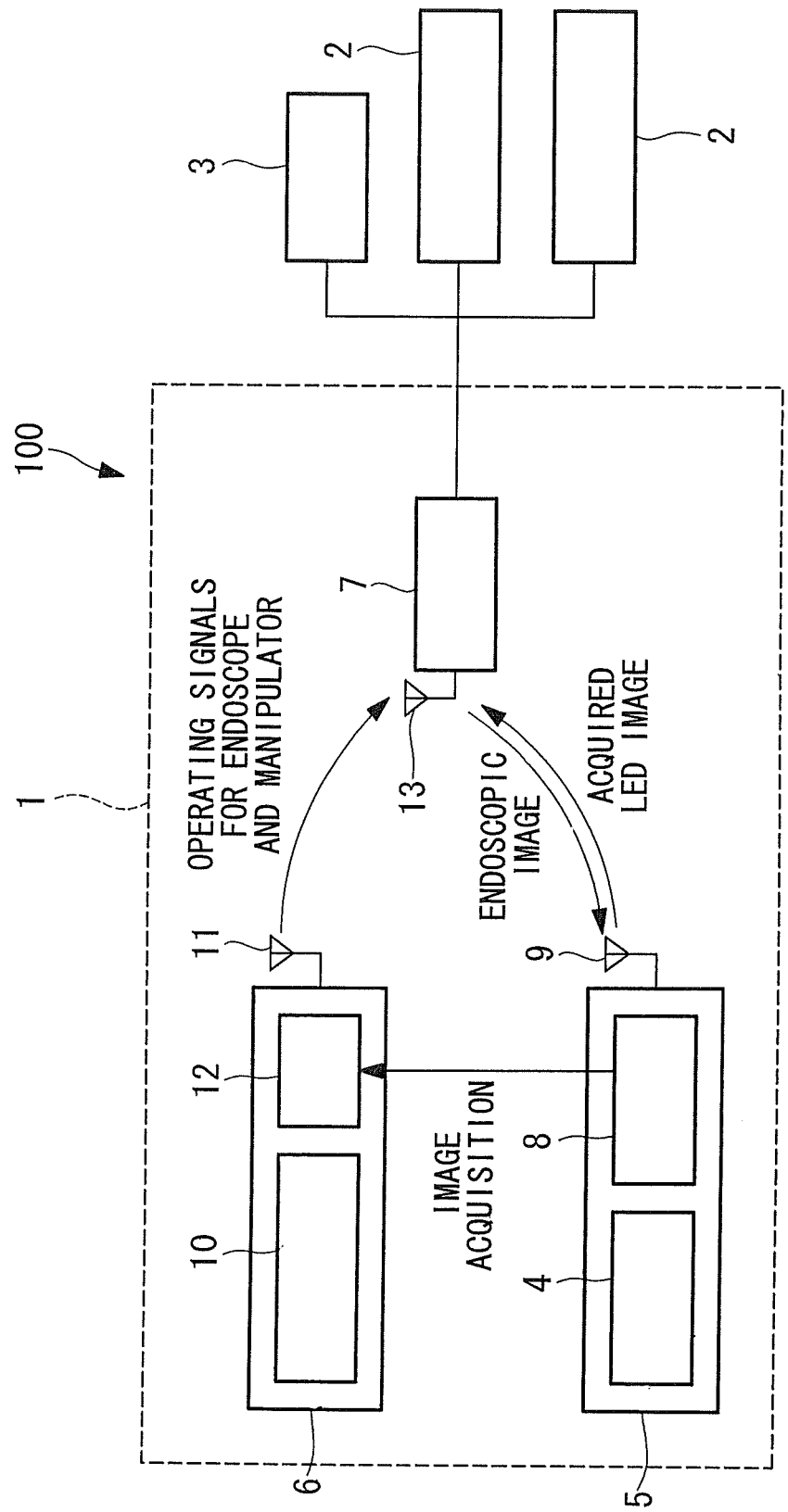
FIG. 2 is a functional block diagram of the operation input unit and the manipulator system in FIG. 1.

The HMD 5 is configured such that the display section 4 is disposed in front of the eyes of the operator B, with the HMD 5 mounted on the head C of the operator B. As shown in FIG. 2, the HMD 5 is equipped with an image acquisition section (relative-position detecting section) 8, such as a CCD, and a transmitting/receiving unit 9 that wirelessly transmits an image signal acquired by the image acquisition section 8. The image acquisition section 8 has a field of view capable of acquiring an image of the region in front of the head C of the operator B, with the HMD 5 mounted on the head C of the operator B.

Figure 3:
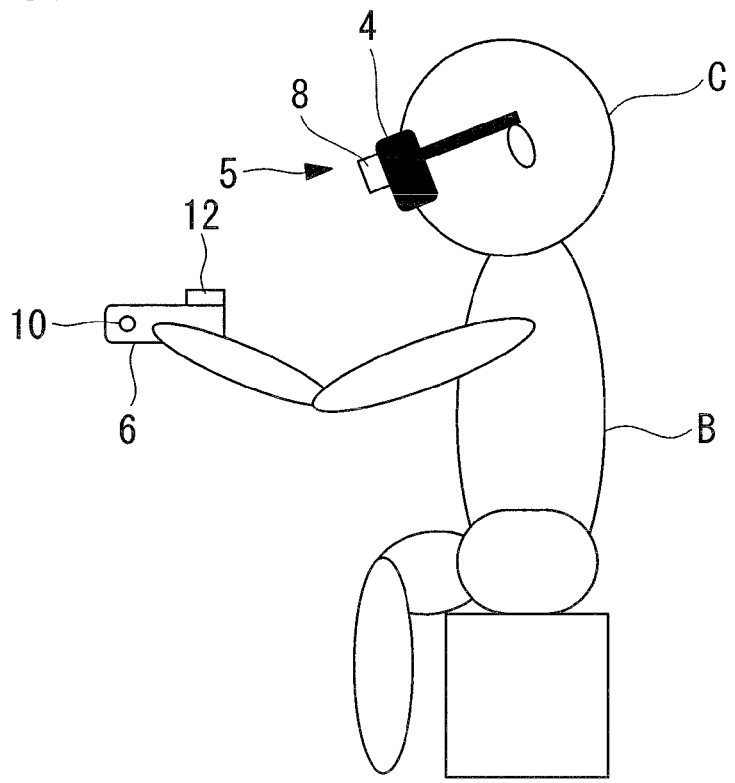
FIG. 3 is a diagram showing the normal operating state of an operator.

The operating unit 6 is configured such that operating signals for the manipulator 2 and the endoscope 3 are input when the operator B operates the operating unit 6 with it held in his or her hand. As shown in FIG. 3, in a normal operating state, the operator B operates the operating unit 6, with the operating unit 6 disposed toward the front with respect to his or her body and his or her face pointing in the direction of the operating unit 6. At that time, the operating unit 6 is disposed on an extension of his or her line of sight when the operator B points his or her line of sight to the display section 4. Thus, the position and orientation of the manipulator 2 with respect to the endoscope 3 match the position and orientation of the operating unit 6 with respect to the display section 4 on which an image of the endoscope 3 is displayed. In other words, the operator B can manipulate the manipulator 2 in a desired direction.

The operating unit 6 is equipped with an enable button 10 (enabling section) that, when pressed, outputs to the control unit 7 an enable signal that enables movement of the manipulator 2. The enable button 10 is covered with, for example, a cover (not shown), so as not to be pressed unless the cover is removed by an operation of the operator B.

The operating signals for the manipulator 2 and the endoscope 3 input to the operating unit 6 and the enable signal for manipulating the manipulator 2 are wirelessly transmitted by a transmitting unit 11.

Figure 4:
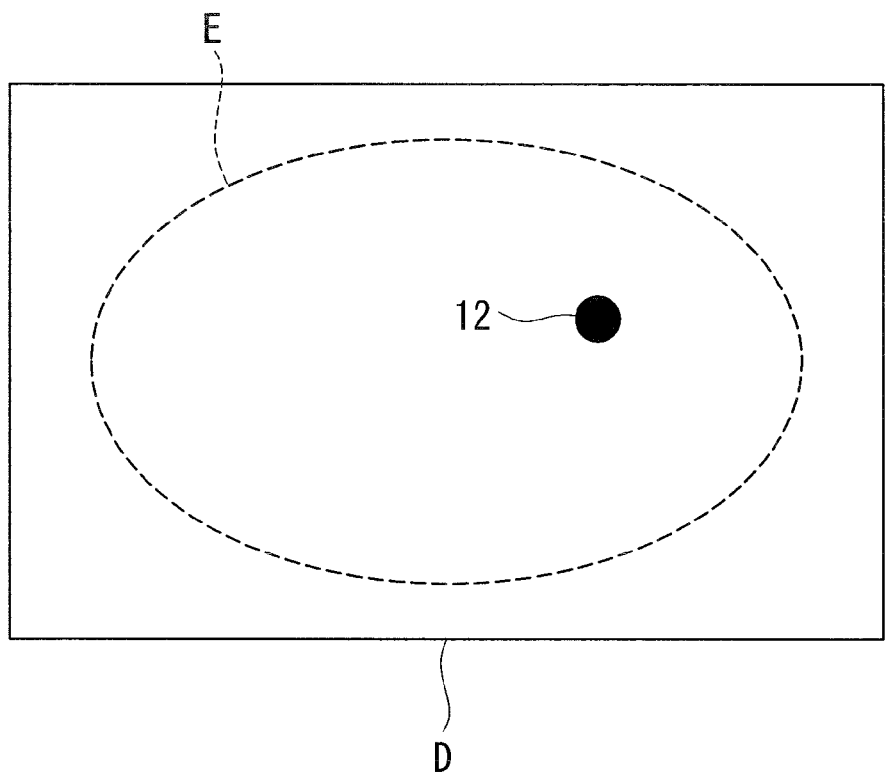
FIG. 4 is a diagram showing an image acquired by an image acquisition section in the normal operating state in FIG. 3.
Figure 5:
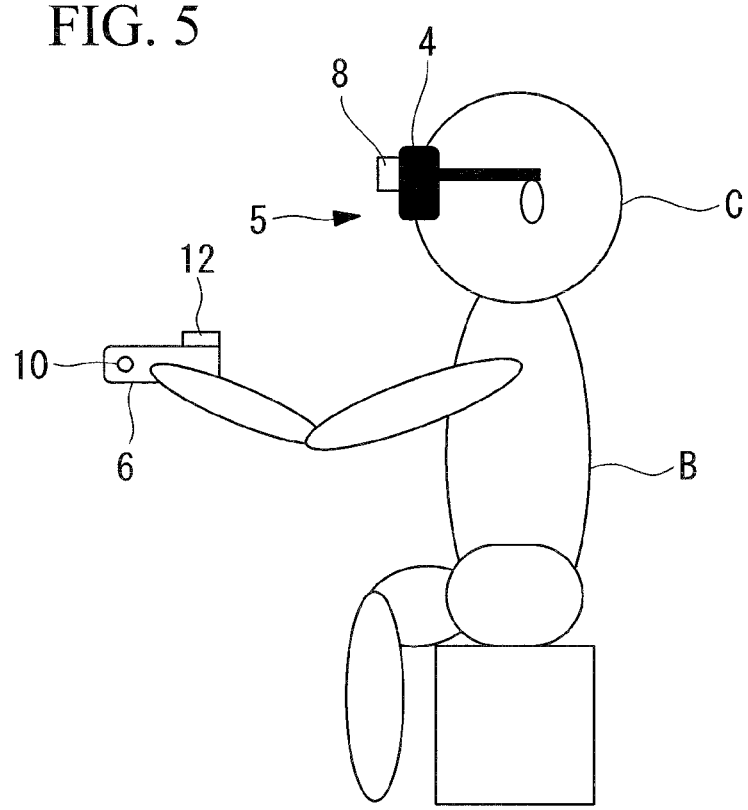
FIG. 5 is a diagram showing an improper operating state of the operator.
Figure 6:
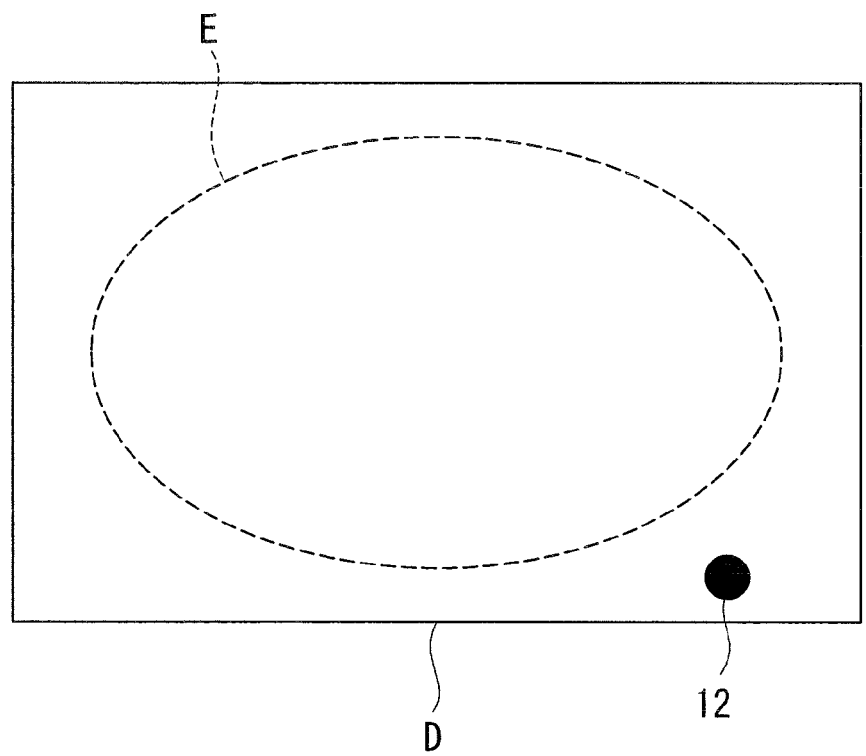
FIG. 6 is a diagram showing an image acquired by the image acquisition section in the improper operating state in FIG. 5.

An LED (relative-position detecting section or index) 12 is fixed to the operating unit 6. When the operator B is in a normal operating state, the LED 12 is present in the vicinity of the center of an image D acquired by the image acquisition section 8, as shown in FIG. 4. On the other hand, as shown in FIG. 5, when the operator B comes out of a normal operating state by changing the orientation of his or her face or dropping the operating unit 6, so that the relative position between the HMD 5 and the operating unit 6 moves, the LED 12 in the image D moves outward from the vicinity of the center, as shown in FIG. 6, or the LED 12 disappears from the image D.

The control unit 7 is equipped with a transmitting/receiving unit 13 that processes an image signal acquired by the endoscope 3 when the image signal is input and transmits it to the HMD 5. The control unit 7 is configured to display the acquired endoscopic image on the display section 4 provided at the HMD 5.

The control unit 7 receives operating signals and an image signal wirelessly transmitted from the operating unit 6 and the HMD 5, respectively, via the transmitting/receiving unit 13. Then, the control unit 7 generates control signals that move the manipulator 2 and the endoscope 3 or changes the operating states thereof by actuating the motors 2a and 3a on the basis of the received operating signals and image signal.

Specifically, the control unit 7 extracts the LED 12 from the image D acquired by the image acquisition section 8. If the LED 12 is present in a predetermined area E, the control unit 7 controls the manipulator 2 in a first control mode. On the other hand, if the LED 12 is not present in the predetermined area E, the control unit 7 controls the manipulator 2 in a second control mode.

Here, the first control mode is a control mode in which a control signal for the manipulator 2 is generated in response to an operating signal for the manipulator 2 transmitted from the operating unit 6. The second control mode is a control mode in which the manipulator 2 is forcedly halted, independently of an operating signal for the manipulator 2 transmitted from the operating unit 6.

The control unit 7 is configured to return to the first control mode when receiving an enable signal from the operating unit 6, with the LED 12 disposed in the predetermined area E in the image D, after switching from the first control mode to the second control mode.

Figure 7:
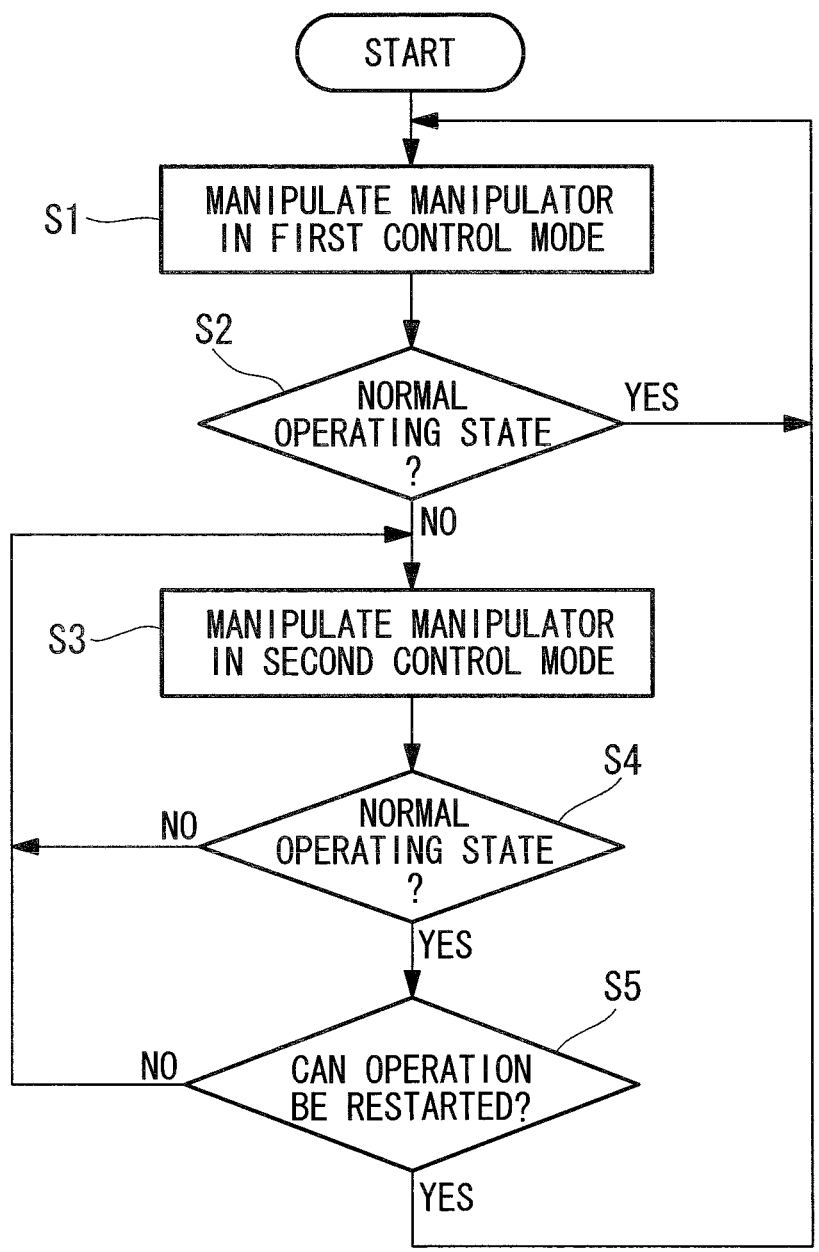
FIG. 7 is a flowchart illustrating the operation of the operation input unit in FIG. 1.

The operation of the thus-configured operation input unit 1 and manipulator system 100 will be described below with reference to the flowchart in FIG. 7.

To perform a surgical procedure using the manipulator system 100 according to this embodiment, the operator B wears the HMD 5 on his or her head C and points his or her face at the operating unit 6, with the hand-held operating unit 6 disposed in front. This allows the operator B to manipulate the endoscope 3 and the manipulator 2 at will with the operating unit 6 while viewing an endoscopic image displayed on the display section 4 (step S1).

If the position of the LED 12 in the image D goes out of the predetermined area E because the operator B changes his or her posture or drops the operating unit 6 while manipulating the endoscope 3 and the manipulator 2 (step S2), the operation input unit 1 detects that the operator B is no longer in a normal operating state. Thus, the operation input unit 1 switches to the second control mode to forcedly halt the manipulator 2 (step S3). Thereafter, the manipulator 2 is maintained in the halted state until the operator B returns to the normal operating state again (step S4) and presses the enable button 10 (step S5).

Thus, according to this embodiment, when the face of the operator B and the operating unit 6 are no longer in an opposing state, this is detected rapidly and with high accuracy from the relative position between the HMD 5 and the operating unit 6, and the motion of the manipulator 2 is halted. This offers the advantage of preventing the manipulator 2 from performing unintended motion due to an unexpected operation of the operating unit 6, for example, even if the operating unit 6 is operated in an unintended direction in a state in which the operator B faces a direction other than the operating unit 6, or even if the operating unit 6 is operated when dropping from his or her hand and coming into contact with the floor or the like. The above advantage is remarkable particularly when the operating range of the operating unit 6 is not limited by a link etc. or the display section 4 is not fixed to space, as in this embodiment.

Furthermore, returning to the first control mode after the manipulator 2 is temporarily forcedly halted is performed at desired timing by the operator B. This prevents the manipulator 2 from moving at the same time as the operator B returns to the normal operating state, thus allowing the operator B to restart the manipulation of the manipulator 2 calmly and accurately.

In the above embodiment, the manipulator 2 is forcedly halted in the second control mode; instead, the manipulator 2 may be manipulated at a sufficiently slow moving speed in response to an operating signal for the manipulator 2 transmitted from the operating unit 6. Alternatively, the operator B may be notified that the operator B is not in a normal operating state by displaying a warning on the display section 4 or issuing a warning sound.

This can also prevent unintended motion of the manipulator 2 by preventing the manipulator 2 from moving suddenly or by attracting the attention of the operator B even if the operator B operates the operating unit 6 in an unintended direction.

Furthermore, in the above embodiment, the motion of the manipulator 2 is controlled by switching in two steps, that is, the first control mode and the second control mode; instead, it may be controlled by switching in three or more steps.

Figure 8:
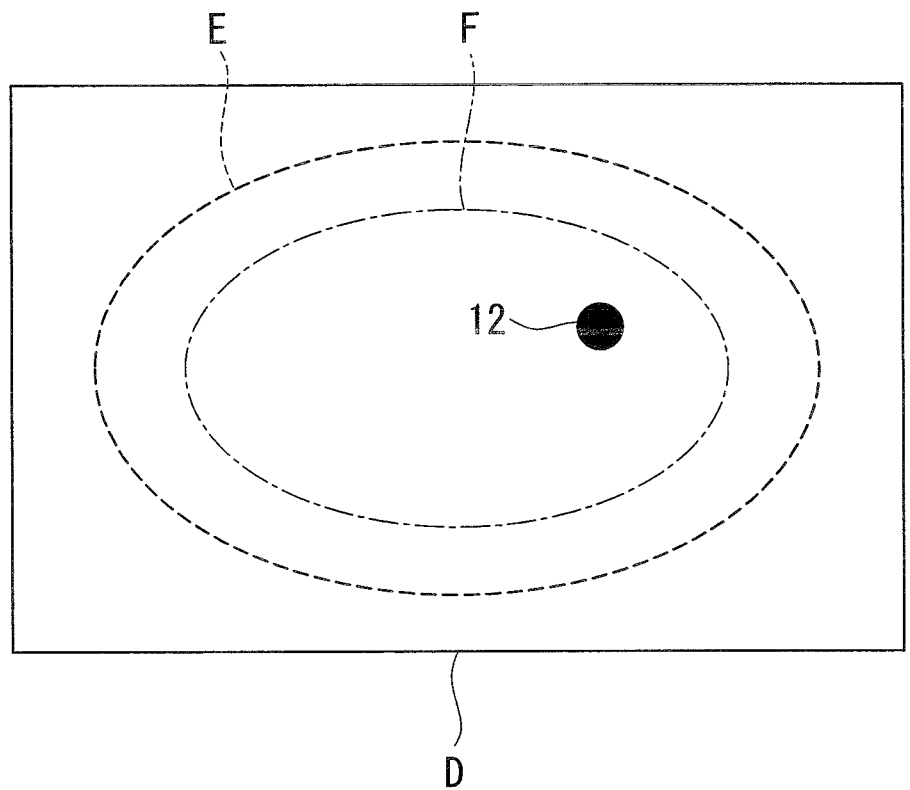
FIG. 8 is a diagram illustrating a modification of the method for controlling the manipulator with the operation input unit in FIG. 1.

For example, as shown in FIG. 8, two or more areas (two areas E and F in the illustrated example) are set in the image D acquired by the image acquisition section 8. When the position of the LED 12 goes out of the area F, the control unit 7 may switch to the second control mode, and when the position of the LED 12 goes further out of the area E, the control unit 7 may switch to a third control mode.

In this case, in the second control mode, the control unit 7 notifies the operator B that the operator B is not in a normal operating state, for example, by slowing the moving speed of the manipulator 2 or by displaying a warning on the display section 4 or sounding a buzzer. In the third control mode, the control unit 7 forcedly halts the manipulator 2, as in the second control mode in the above embodiment.

This can prevent the manipulator 2 from being frequently forcedly halted due to a small motion of the operator B, which would unnecessarily hinder the progress of the surgical procedure.

In the above embodiment, the image acquisition section 8 is provided at the HMD 5, and the LED 12 is provided at the operating unit 6; instead, the image acquisition section 8 may be provided at the operating unit 6, and the LED 12 may be provided at the HMD 5.

This also allows the relative position between the head C of the operator B and the operating unit 6 to be detected.

Next, an operation input unit 1 and a manipulator system 100 according to a second embodiment of the present invention will be described below with reference to FIGS. 9 and 10.

In this embodiment, differences from the first embodiment will be mainly described, and configurations common to the first embodiment are given the same reference numerals, and descriptions thereof will be omitted.

Figure 9:
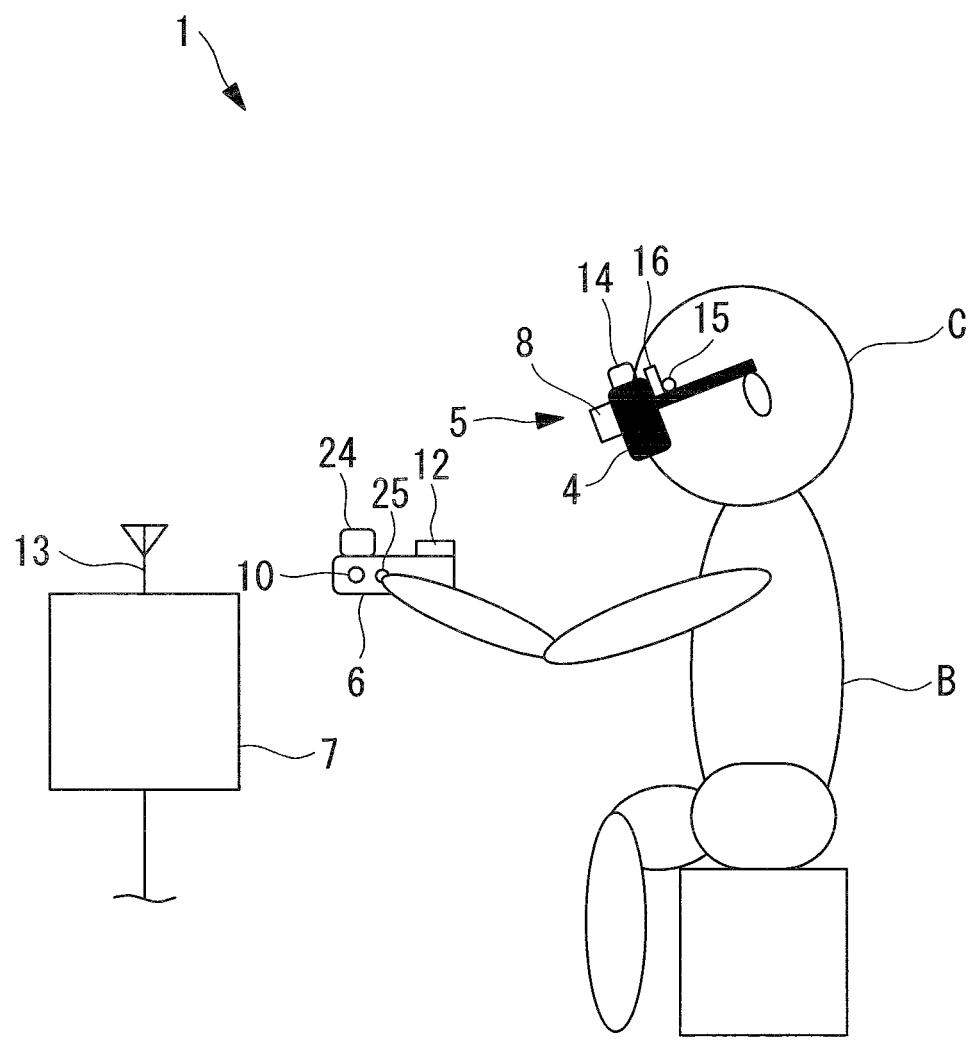
FIG. 9 is a diagram showing the overall configuration of an operation input unit according to a second embodiment of the present invention.

As shown in FIG. 9, the operation input unit 1 according to this embodiment differs from the first embodiment in that it is equipped with acceleration sensors (relative-position detecting sections) 14 and 24 and contact sensors 15 and 25 provided at the HMD 5 and the operating unit 6, respectively, and a line-of-sight sensor 16 provided at the HMD 5.

The acceleration sensors 14 and 24 detect accelerations in three different directions.

The contact sensor 15 provided at the HMD 5 is disposed at a position at which it comes into contact with the head C of the operator B when the operator B wears the HMD 5 properly. The contact sensor 25 provided at the operating unit 6 is disposed at a position at which it comes into contact with the hand of the operator B when the operator B holds the operating unit 6 properly.

The line-of-sight sensor 16 detects the line of sight of the operator B.

Figure 10:
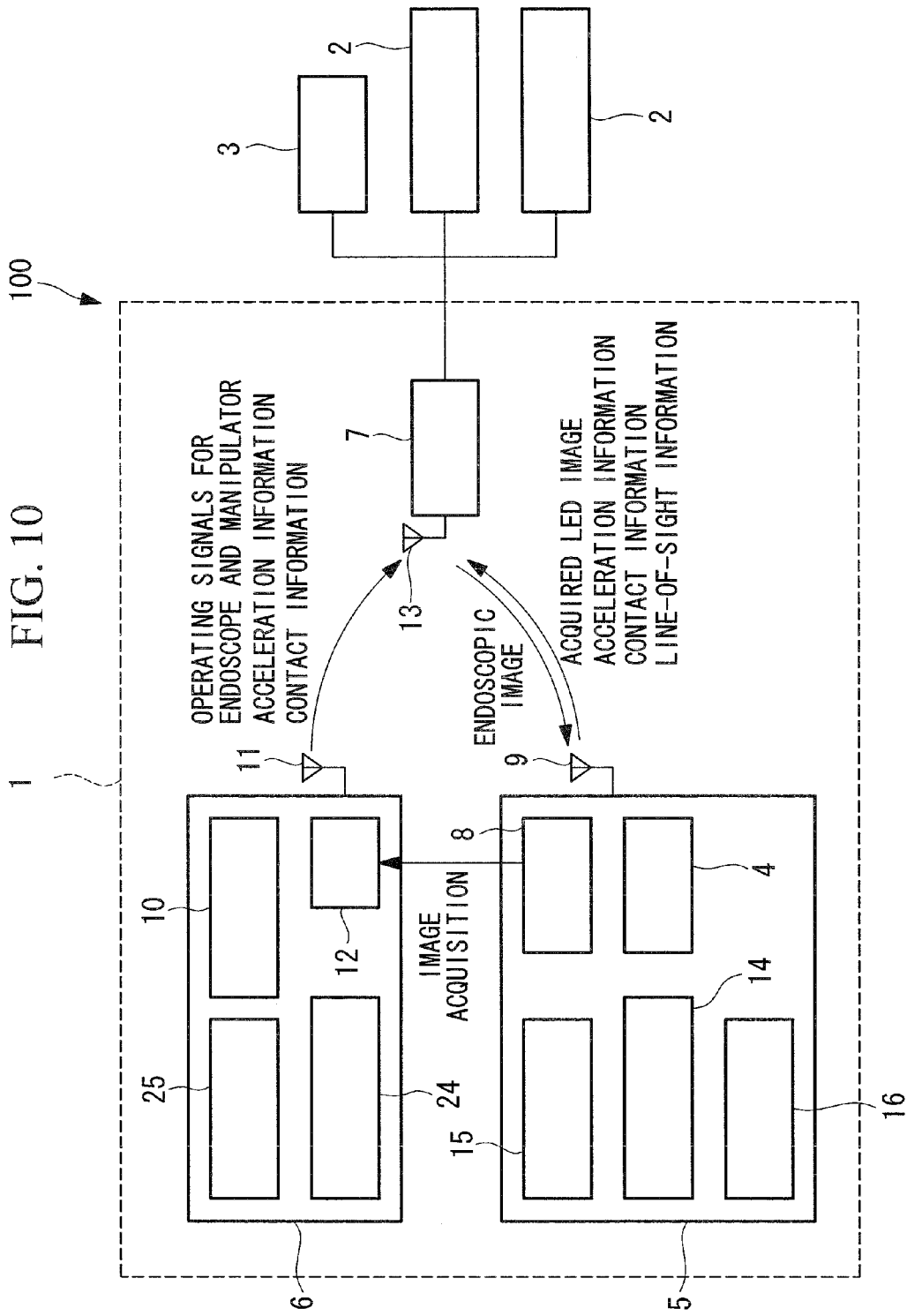
FIG. 10 is a functional block diagram of the operation input unit and the manipulator system in FIG. 9.

Information on the accelerations, whether or not there is contact, and the line of sight detected by the individual sensors 14, 15, 16, 24, and 25 is transmitted to the control unit 7 by the transmitting/receiving unit 9 or the transmitting unit 11, as shown in FIG. 10.

The control unit 7 switches to the second control mode when the level of acceleration detected by at least one of the acceleration sensors 14 and 24 is higher than a predetermined threshold value. Thus, the rapid motion of the HMD 5 or the operating unit 6 when the operator B turns his or her face or drops the operating unit 6 can be detected, and the manipulator 2 can be forcedly halted.

The control unit 7 calculates displacements by determining the second-order integrals of accelerations detected by the individual acceleration sensors 14 and 24 for individual directions after the operation of the operating unit 6 is started. Then, the control unit 7 integrates the calculated displacements to thereby detect the current position of the HMD 5 in a three-dimensional space relative to the operating unit 6.

The control unit 7 switches from the first control mode to the second control mode when the LED 12 is not present in the predetermined area E of the image D acquired by the image acquisition section 8 and when the relative position between the HMD 5 and the operating unit 6 detected from the accelerations detected by the acceleration sensors 14 and 24 goes out of a predetermined range, with the operator B in a normal operating state.

Furthermore, the control unit 7 switches from the first control mode to the second control mode when the contact state of the operator B with the head C or the hand becomes undetected by the contact sensor 15 or 25 after the operation of the operating unit 6 is started. This allows quick detection of displacement of the HMD 5 that would hinder the operator B from normally observing the display section 4 or separation of the operating unit 6 from the hand of the operator B, thus forcedly halting the manipulator 2.

Furthermore, the control unit 7 switches from the first control mode to the second control mode when the angle of the line of sight detected by the line-of-sight sensor 16 with respect to the front direction of the operator B becomes larger than a threshold value. Thus, when the line of sight of the operator B deviates from the direction of the display section 4, it is detected, and the manipulator 2 is forcedly halted.

The operation of the thus-configured manipulator system 100 will be described below.

To perform a surgical procedure using the manipulator system 100 according to this embodiment, the operator B wears the HMD 5 and holds the operating unit 6 by hand and manipulates the endoscope 3 and the manipulator 2 as in the first embodiment. When the operator B releases the operating unit 6 or removes the HMD 5 from his or her head C because of the occurrence of an abnormality in outside the field of view or for another reason or when the operator B turns his or her face when talked to by a person in the vicinity, the manipulator 2 is forcedly halted. The manipulator 2 remains halted until the operator B returns to the normal state and presses the enable button 10.

This also allows quick detection of a state in which the operator B cannot normally operate the operating unit 6, as in the first embodiment, thus preventing the manipulator 2 from performing unintended motion due to an unexpected operation of the operating unit 6.

Furthermore, the relative position between the HMD 5 and the operating unit 6 is detected in duplicate by the image acquisition section 8 and LED 12, and by the acceleration sensors 14 and 24. Thus, for example, even if one of the image acquisition section 8 and the LED 12 or the acceleration sensors 14 and 24 comes out of a normal state, such as when an object is interposed between the HMD 5 and the operating unit 6 to hide the LED 12 from the image acquisition section 8, so that the LED 12 disappears suddenly from the image D acquired by the image acquisition section 8, the relative position between the HMD 5 and the operating unit 6 can be accurately detected. Accordingly, this can prevent problems such as the manipulator 2 being unnecessarily halted even though the operator B normally operates the operating unit 6, thus allowing the manipulator 2 to be appropriately controlled.

In the above embodiment, instead of the acceleration sensors 14 and 24, gyro sensors (relative-angle detecting sections) may be adopted. The gyro sensors detect angular velocities in three different directions.

In this case, the control unit 7 switches to the second control mode when an angular velocity detected by at least one of the gyro sensors is larger than a predetermined threshold value. Furthermore, the control unit 7 calculates rotation angles by determining the first-order integrals of the angular velocities detected by the individual gyro sensors for the individual directions. The control unit 7 integrates the calculated rotation angles to thereby detect the current relative orientation between the HMD 5 and the operating unit 6.

The control unit 7 switches from the first control mode to the second control mode when the LED 12 is not present in the predetermined area E in the image D acquired by the image acquisition section 8 and when the relative orientation between the operating unit 6 and the HMD 5 calculated from the angular velocities detected by the gyro sensors deviates from a predetermined orientation.

This also allows rapid detection of the quick motion of the HMD 5 or the operating unit 6, thus allowing accurate detection of whether the HMD 5 and the operating unit 6 are in an appropriate positional relationship.

Figure 11:
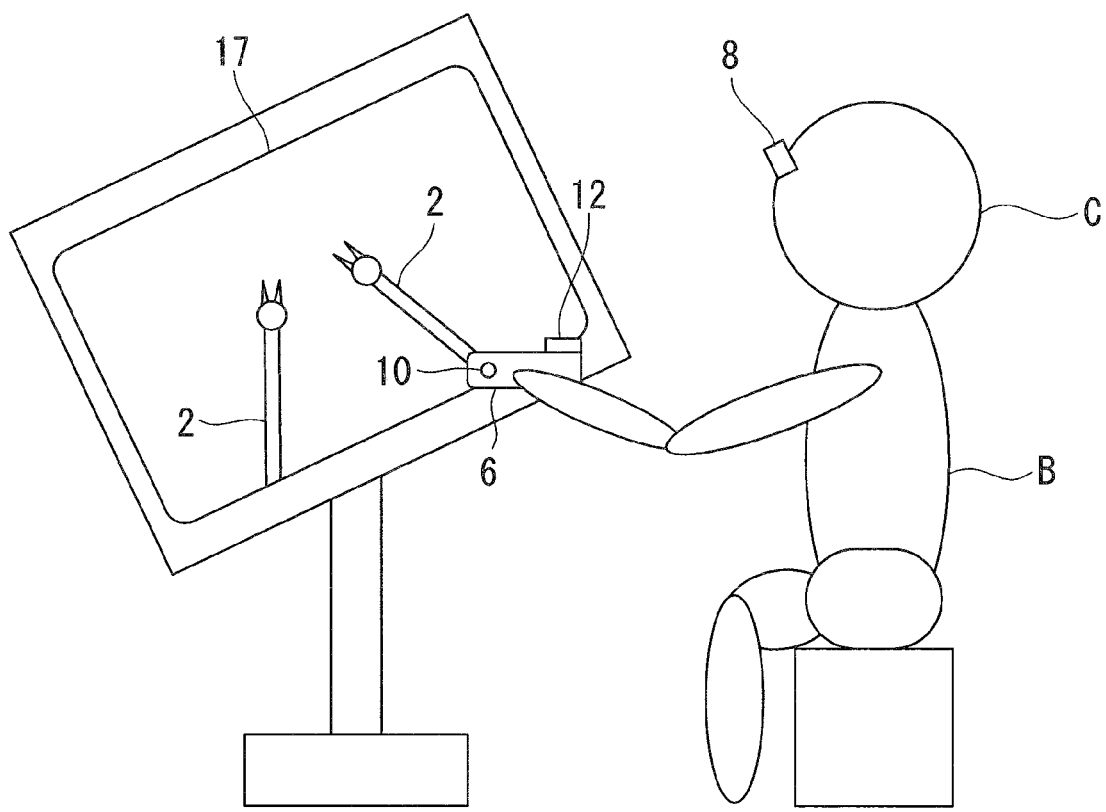
FIG. 11 is a diagram showing a modification of the operation input units in FIGS. 1 and 9, in which a separate display is used.

In the first and second embodiments described above, the HMD 5 in which the display section 4 and the head-mounted unit are integrally provided is exemplified; instead, as shown in FIG. 11, a head-mounted unit and a separate display 17 may be adopted. 3D glasses for a separate 3D display unit may be adopted as a head-mounted unit. The sensors 14, 15, 16, 24, and 25 in the second embodiment can be appropriately provided at the head C of the operator B or at the operating unit 6.

This also allows quick detection of a state in which the operator B becomes unable to normally operate the operating unit 6 because the operator B suddenly changes his or her posture or releases the operating unit 6, thus preventing unintended motion of the manipulator 2.

The present invention has the following aspects.

A first aspect of the present invention is an operation input unit including a display; a head-mounted unit mounted on the head of an operator; an operating unit to which an operating signal for a displayed object displayed on the display is input by the operation of the operator; a relative-position detecting section that detects the relative position between the head-mounted unit and the operating unit; and a control unit that controls the displayed object by switching between a first control mode in which the motion of the displayed object is controlled in accordance with an operating signal input to the operating unit and a second control mode in which the motion of the displayed object is controlled by limiting an operating signal input to the operating unit, on the basis of the relative position detected by the relative-position detecting section.

According to the first aspect of the present invention, an operator who wears the head-mounted unit can operate a displayed object on the display at will with the hand-held operating unit while viewing the display in the first control mode. In this case, when the operator or the operating unit moves for some reason, the relative position detected by the relative-position detecting section changes, so that the control unit switches to the second control mode. This allows quick detection of a state in which the operator becomes unable to normally operate the operating unit and limits the motion of the displayed object independently of the operating signal input to the operating unit, thus preventing unintended motion of the displayed object due to an unexpected operation of the operating unit.

In the first aspect, the control unit may switch from the first control mode to the second control mode when the relative position between the head-mounted unit and the operating unit goes out of a predetermined range.

This allows more accurate detection of a state in which the operator and the operating unit come out of the normal operating state by setting a range in which the displayed object is positioned by the operator in the normal operating state as the predetermined range, thereby allowing the operation on the displayed object by means of the operating unit to be limited.

In the first aspect, the relative-position detecting section may include an index provided at one of the operating unit and the head-mounted unit; and an image acquisition section that is provided at the other of the operating unit and the head-mounted unit and that acquires the index; and the control unit may switch between the first control mode and the second control mode on the basis of the position of the index in an image acquired by the image acquisition section.

This allows the relative position between the head-mounted unit and the operating unit to be detected with a simple configuration.

In the first aspect, the relative-position detecting section may include space sensors that are provided individually at the head-mounted unit and the operating unit and that detect displacement information in the space coordinate system thereof; and the control unit may switch from the first control mode to the second control mode when the relative position between the head-mounted unit and the operating unit obtained by the space sensors goes out of a predetermined range.

This allows the relative position between the head-mounted unit and the operating unit to be detected with a simple configuration.

In the first aspect, the relative-position detecting section may include space sensors that are provided individually at the head-mounted unit and the operating unit and that detect displacement information in the space coordinate system thereof; and the control unit may switch from the first control mode to the second control mode when displacement information detected by at least one of the space sensors is larger than a predetermined threshold value.

This allows deviation of the relative position due to the movement of the head-mounted unit or the operating unit to be detected with a simple configuration. Furthermore, in the case where the index and the image acquisition section are used in combination, it can be accurately determined whether the operator is in a normal operating state even if the index, the image acquisition section, or the space sensors comes out of a normal operating state, thereby appropriately controlling the displayed object.

In the first aspect, a relative-angle detecting section that detects the relative angle between the head-mounted unit and the operating unit may be provided; wherein the control unit may switch from the first control mode to the second control mode when the relative angle detected by the relative-angle detecting section is larger than a predetermined threshold.

This allows the relative orientation between the head-mounted unit and the operating unit to be detected, thus allowing more accurate detection of the relative movement thereof.

In the first aspect, a contact sensor that is provided at the operating unit and that detects whether the operating unit and the hand of the operator are in contact may be provided; wherein the control unit may switch from the first control mode to the second control mode when contact between the operating unit and the hand of the operator is not detected by the contact sensor.

This allows the operation of the displayed object by means of the operating unit to be limited when the operating unit is not appropriately held in the hand of the operator.

In the first aspect, a contact sensor that is provided at the head-mounted unit and that detects whether the head-mounted unit and the head of the operator are in contact may be provided; wherein the control unit may switch from the first control mode to the second control mode when contact between the head-mounted unit and the head of the operator is not detected by the contact sensor.

This allows the operation of the displayed object by mean of the operating unit to be limited when the head-mounted unit is not appropriately mounted on the head of the operator.

In the first aspect, a line-of-sight detecting section that detects the line of sight of the operator may be provided; wherein the control unit may switch from the first control mode to the second control mode when the line of sight detected by the line-of-sight detecting section deviates from the front direction of the operator.

This allows the operation of the displayed object by means of the operating unit to be limited when the operator views in a direction deviated from the display disposed in front.

In the first aspect, an enabling section that permits the control unit to switch from the second control mode to the first control mode by the operation of the operator may be provided; wherein the control unit may switch to the first control mode when permitted by the enabling section after switching from the first control mode to the second control mode.

This allows the limitation with respect to the motion of the displayed object to be cancelled at a desired timing after the operator returns to the normal operating state, after switching to the second control mode.

A second aspect of the present invention is a manipulator system including the operation input unit described in one of the above; a manipulator that is the displayed object; and an observation unit that acquires an image of the displayed object to be displayed on the display.

What is claimed is:

1. An operation input unit comprising:
    a display;
    a head-mounted unit mounted on the head of an operator;
    an operating unit to which an operating signal for a displayed object displayed on the display is input by the operation of the operator;
    a relative-position detecting section that detects the relative position between the head-mounted unit and the operating unit; and
    a control unit that controls the displayed object by switching between a first control mode and a second control mode and between the second control mode and a third control mode, on the basis of the relative position detected by the relative-position detecting section;
    wherein, in the first control mode, the motion of the displayed object is controlled in accordance with an operating signal input to the operating unit;
    wherein, in the second control mode, the motion of the displayed object is controlled by limiting an operating signal input to the operating unit; and
    wherein, in the third control mode, the motion of the displayed object is controlled to be stopped regardless of an operating signal input to the operating unit;
    wherein the control unit switches from the first control mode to the second control mode when the relative position between the head-mounted unit and the operating unit goes out of a first predetermined range but remains within a second predetermined range and the control unit switches from the second control mode to the third control mode when the relative position between the head-mounted unit and the operating unit goes out of the second predetermined range, the second predetermined range being greater than the first predetermined range.

2. The operation input unit according to claim 1, wherein the relative-position detecting section includes an index provided at one of the operating unit and the head-mounted unit; and an image acquisition section that is provided at the other of the operating unit and the head-mounted unit and that acquires the index; and
    the control unit switches between the first control mode and the second control mode and between the second control mode and the third control mode on the basis of the position of the index in an image acquired by the image acquisition section, the first predetermined range being a first area of the image and the second predetermined range being a second area of the image, the second area being outside the first area.

3. The operation input unit according to claim 2, wherein the relative-position detecting section includes space sensors that are provided individually at the head-mounted unit and the operating unit and that detect displacement information in the space coordinate system thereof; and
    the control unit switches from one of the first, second and third control modes to another of the first, second and third control modes when the relative position between the head-mounted unit and the operating unit obtained by the space sensors goes out of the corresponding first or second predetermined range.

4. The operation input unit according to claim 2, wherein the relative-position detecting section includes space sensors that are provided individually at the head-mounted unit and the operating unit and that detect displacement information in the space coordinate system thereof; and
    the control unit switches from one of the first, second and third control modes to another of the first, second and third control modes when displacement information detected by at least one of the space sensors is larger than a predetermined threshold value.

5. A manipulator system comprising:
    the operation input unit according to claim 2;
    a manipulator that is the displayed object; and
    an observation unit that acquires an image of the displayed object to be displayed on the display.

6. The operation input unit according to claim 1, wherein the relative-position detecting section includes space sensors that are provided individually at the head-mounted unit and the operating unit and that detect displacement information in the space coordinate system thereof; and
    the control unit switches from one of the first, second and third control modes to another of the first, second and third control modes when the relative position between the head-mounted unit and the operating unit obtained by the space sensors goes out of the corresponding first or second predetermined range.

7. A manipulator system comprising:
    the operation input unit according to claim 6;
    a manipulator that is the displayed object; and
    an observation unit that acquires an image of the displayed object to be displayed on the display.

8. The operation input unit according to claim 1, wherein the relative-position detecting section includes space sensors that are provided individually at the head-mounted unit and the operating unit and that detect displacement information in the space coordinate system thereof; and
    the control unit switches from one of the first, second and third control modes to another of the first, second and third control modes when displacement information detected by at least one of the space sensors is larger than a predetermined threshold value.

9. A manipulator system comprising:
    the operation input unit according to claim 8;
    a manipulator that is the displayed object; and
    an observation unit that acquires an image of the displayed object to be displayed on the display.

10. The operation input unit according to claim 1, further comprising:
    a relative-angle detecting section that detects the relative angle between the head-mounted unit and the operating unit;
    wherein the control unit switches from one of the first, second and third control modes to another of the first, second and third control modes when the relative angle detected by the relative-angle detecting section is larger than a predetermined threshold.

11. A manipulator system comprising:
the operation input unit according to claim 8;
a manipulator that is the displayed object; and
an observation unit that acquires an image of the displayed object to be displayed on the display.

12. The operation input unit according to claim 1, further comprising:
a contact sensor that is provided at the operating unit and that detects whether the operating unit and the hand of the operator are in contact;
wherein the control unit switches from one of the first, second and third control modes to another of the first, second and third control modes when contact between the operating unit and the hand of the operator is not detected by the contact sensor.

13. A manipulator system comprising:
the operation input unit according to claim 12;
a manipulator that is the displayed object; and
an observation unit that acquires an image of the displayed object to be displayed on the display.

14. The operation input unit according to claim 1, further comprising:
a contact sensor that is provided at the head-mounted unit and that detects whether the head-mounted unit and the head of the operator are in contact;
wherein the control unit switches from one of the first, second and third control modes to another of the first, second and third control modes when contact between the head-mounted unit and the head of the operator is not detected by the contact sensor.

15. A manipulator system comprising:
the operation input unit according to claim 14;
a manipulator that is the displayed object; and
an observation unit that acquires an image of the displayed object to be displayed on the display.

16. The operation input unit according to claim 1, further comprising:
a line-of-sight detecting section that detects the line of sight of the operator;
wherein the control unit switches from one of the first, second and third control modes to another of the first, second and third control modes when the line of sight detected by the line-of-sight detecting section deviates from a front direction.

17. A manipulator system comprising:
the operation input unit according to claim 16;
a manipulator that is the displayed object; and
an observation unit that acquires an image of the displayed object to be displayed on the display.

18. The operation input unit according to claim 1, further comprising:
an enabling section that permits the control unit to switch from the third control mode to the first control mode by the operation of the operator;
wherein the control unit switches to the first control mode when permitted by the enabling section after switching from the first control mode to the third control mode.

19. A manipulator system comprising:
the operation input unit according to claim 1;
a manipulator that is the displayed object; and
an observation unit that acquires an image of the displayed object to be displayed on the display.

20. The operation input unit according to claim 1, wherein in the second control mode, the motion of the displayed object is controlled by limiting the operation signal input to the operating unit and the operator is notified that the control unit does not operate in the first control mode.

* * * * *